United States Patent
Perkins et al.

(10) Patent No.: US 11,752,311 B2
(45) Date of Patent: Sep. 12, 2023

(54) APPARATUS AND METHODS FOR RESTORING TISSUE

(71) Applicant: Alucent Biomedical, Inc., Salt Lake City, UT (US)

(72) Inventors: D H Perkins, Woods Cross, UT (US); Calvin Turland, Montreal (CA); Teresa Mihalik, Montreal (CA); Rany Pea, Montreal (CA)

(73) Assignee: Alucent Biomedical, Inc., Salt Lake City, UT (US)

( * ) Notice: Subject to any disclaimer, the term of this patent is extended or adjusted under 35 U.S.C. 154(b) by 385 days.

(21) Appl. No.: 17/010,092

(22) Filed: Sep. 2, 2020

(65) Prior Publication Data
US 2022/0062598 A1    Mar. 3, 2022

(51) Int. Cl.
*A61M 25/10*    (2013.01)

(52) U.S. Cl.
CPC ...... *A61M 25/1011* (2013.01); *A61M 25/104* (2013.01); *A61M 25/1025* (2013.01); *A61M 2025/105* (2013.01); *A61M 2025/1086* (2013.01); *A61M 2205/05* (2013.01)

(58) Field of Classification Search
CPC .... A61M 2025/1086; A61M 2025/105; A61M 2025/1013
See application file for complete search history.

(56) References Cited

U.S. PATENT DOCUMENTS

| | | | |
|---|---|---|---|
| 10,737,075 B2 | 8/2020 | Cottone et al. | |
| 2018/0147394 A1* | 5/2018 | Spindler | A61M 25/1002 |
| 2019/0174995 A1 | 6/2019 | Fukushima et al. | |
| 2020/0101269 A1* | 4/2020 | Hayes | A61B 17/12136 |

OTHER PUBLICATIONS

Dictionary.com, "Translucent", https://www.dictionary.com/browse/translucent (Year: 2022).*
Dictionary.com, "Transparent", https://www.dictionary.com/browse/transparent (Year: 2022).*
International Search Report and Written Opinion of the International Searching Authority in corresponding International Application No. PCT/US2021/48855 dated Dec. 14, 2021.

* cited by examiner

*Primary Examiner* — Theodore J Stigell
*Assistant Examiner* — Rachel T. Smith
(74) *Attorney, Agent, or Firm* — Finnegan, Henderson, Farabow, Garrett & Dunner, LLP

(57) ABSTRACT

An apparatus and methods tissue restoration are provided. The apparatus may include a catheter shaft extending from a proximal end to a distal tip, a plurality of serial balloons positioned on a translucent distal segment of the catheter shaft proximal to the distal tip and positioned inside of and concentric with a second distal balloon, the plurality of serial balloons in fluid communication with an inflation source via a first lumen, each of the plurality of serial balloons having a selectively expandable outermost radial surface. The plurality of serial balloons may include a translucent material, a series of isolated volumetric regions positioned between the plurality of serial balloons and recessed from the outermost radial surfaces of the serial balloons. The apparatus may include a distal balloon positioned around the plurality of serial balloons, and a light fiber positioned in the catheter shaft and extending through the translucent distal segment.

20 Claims, 9 Drawing Sheets

APPARATUS AND METHODS FOR RESTORING TISSUE

BACKGROUND

Technical Field

The present disclosure generally relates to apparatus and methods to restore a tissue's function. More particularly, and without limitation, the disclosed embodiments relate to catheters, and catheter systems to create a natural vessel scaffolding and restore tissue function.

Background Description

Balloon catheters are used in a number of surgical applications including occluding blood flow either distally or proximally of a treatment site. The inflation of the balloon must be controlled in order to avoid over-expansion or breakage of the balloon, which may rupture or otherwise damage the vessel. Percutaneous Transluminal Angioplasty (PTA), in which a balloon is used to open obstructed arteries, has been widely used to treat atherosclerotic lesions. However, this technique is limited by the vexing problems of re-occlusion and restenosis. Restenosis results from the excessive proliferation of smooth muscle cell (SMC), and the rate of restenosis is above 20%. Thus, about one in five patients treated with PTA must be treated again within several months.

Additionally, stenting is a popular treatment, in which a constricted arteriosclerotic segment of the artery is mechanically expanded with the aid of a balloon catheter, followed by placement of a metallic stent within the vascular lumen to restore the flow of blood. Constriction or occlusion of the artery is problematic and can be itself, or cause, major health complications. Placement of a metallic stent has been found to result in the need for postoperative treatment in 20% to 30% of patients. One cause of this high frequency of required postoperative treatment is vascular intimal hyperplasia within the vascular lumen resulting in lumen narrowing despite the stent being placed. In order to decrease in-stent restenosis, attempts have been made to design a stent of a type having a surface carrying a restenosis-inhibiting drug so that when the stent is placed in an artery, the drug is eluted in a controlled manner within the vascular lumen. Those attempts have led to commercialization of drug-eluting stents (hereinafter referred to as DES) utilizing sirolimus (immunosuppressor) and paclitaxel (cytotoxic antineoplastic drug). However, since those drugs have an effect of inhibiting the proliferation of vascular cells (endothelial cells and smooth muscle cells) by acting on the cell cycle thereof, not only can the vascular intimal hyperplasia resulting from an excessive proliferation of the smooth muscle cells be suppressed, but proliferation is also suppressed of endothelial cells once denuded during placement of the stent. This can result in the adverse effect where the repair or treatment of the intima of a blood vessel becomes reduced. In view of the fact that thrombosis tends to occur more easily at a site less covered with endothelial cells in the intima of a blood vessel, an antithrombotic drug must be administrated for a prolonged time, say, half a year or so and, notwithstanding this antithrombotic drug administration, a risk of late thrombosis and restenosis will occur upon its discontinuance.

EVAR (endovascular aneurysm repair) is another application of a balloon catheter. The balloon catheter is inflated to occlude aortic blood flow before the placement of an aortic stent graft (a self-expanding nitinol frame covered with a membrane material, such as ePTFE, expanded polytetrafluoroethylene) or inside the stent graft after placement for better wall apposition of the stent graft frame and membrane. While this technique has replaced many surgical aortic reconstructions, at times the stent graft may be misshaped for the aorta, may cover and prevents arterial blood flow to necessary side branches, may further damage the aorta during placement, may permit blood to flow around the stent graft, does not treat the underlying causes of aneurysm formation, and is typically placed when the aneurysm has exceeded 5 cm in major diameter. Aneurysms are typically discovered during routine physical examinations and treated with lifestyle changes, such as smoking cessation, and medications for hypercholesteremia and hypertension. This course of action is followed by regular monitoring until the aneurysm grows to a certain size (typically greater than 5 cm in diameter) at which time a stent graft may be placed preventing rupture.

Yet another application of a balloon catheter may be to increase the luminal diameter of the vein in an arteriovenous fistula (AVF) used for hemodialysis. This type of AVF surgically connects a peripheral vein to an adjacent peripheral artery (e.g., in the arm). In response to the constant higher arterial pressure flowing into the lower pressure vein, the vein wall may be damaged, reducing the inside diameter and preventing the flow rates necessary for proper hemodialysis. In an effort to re-establish proper flow rates, a balloon catheter may be inserted to the location of the reduced vein diameter and inflated, increasing the luminal diameter. However, opening the vein diameter is typically temporary, causing further wall damage and not addressing the vein wall structure inadequacies. The vein wall structure permits low pressure blood flow; the higher pressure muscular elastic arterial wall components are absent. This fundamental difference may contribute to the eventual failure of the AVF.

The technical problem addressed by the present disclosure is therefore to overcome these prior art difficulties by creating devices providing for controlled delivery of therapeutic agents to the surrounding tissues, propping the vessel open to a final shape, and functionalizing the therapeutic agent within the tissue and forming the cast shape, permitting blood flow and restoring tissue function. Other technical problems addressed by the present disclosure is a localized drug delivery system for the attenuation of aneurysmal growth and for strengthening a vein wall improving arteriovenous fistula longevity during hemodialysis. The solution to these technical problems is provided by the embodiments described herein and characterized in the claims.

SUMMARY

The embodiments of the present disclosure include catheters, catheter systems, and methods of forming a tissue scaffolding using catheter systems. Advantageously, the exemplary embodiments allow for controlled, uniform delivery of therapeutic agents to the surrounding tissues, casting the tissue to a final shape, and functionalizing the therapeutic agent in the tissue, forming the cast shape and propping the vessel open. The tissue may be a vessel wall of a vessel within the cardiovascular system.

Embodiments of the present disclosure provide an apparatus. The apparatus may include a catheter shaft extending from a proximal end to a distal tip, a plurality of serial balloons positioned on a translucent distal segment of the catheter shaft proximal to the distal tip and positioned inside of and concentric with a second distal balloon, the plurality of serial balloons in fluid communication with an inflation source via a first lumen, each of the plurality of serial balloons having a selectively expandable outermost radial surface. The plurality of serial balloons may include a translucent material, a series of isolated volumetric regions positioned between the plurality of serial balloons and recessed from the outermost radial surfaces of the serial balloons. The apparatus may include a distal balloon positioned around the plurality of serial balloons, and a light fiber positioned in the catheter shaft and extending through the translucent distal segment.

In some embodiments, the distal balloon comprises a plurality of apertures radially aligned with the isolated volumetric regions of the plurality of serial balloons, the apertures selectively communicate the drug from the distal balloon to a treatment area of a subject. The apertures may provide uniform drug delivery to the series of isolated volumetric regions within the treatment area. The plurality of serial balloons may include a plurality of infusion ports, each infusion port is positioned between the plurality of serial balloons. The plurality of serial balloons may remain in an expanded state during drug delivery to the series of isolated volumetric regions.

In some embodiments, during inflation of the distal balloon, the fluid fills between an inside surface of the distal balloon and an outside surface of the infusion ports, filling the isolated volumetric regions. A pressure of the fluid in the isolated volumetric regions may increase and inflate the distal balloon, the increased pressure may deliver the fluid through the apertures.

In some embodiments, the plurality of serial balloons, and the distal balloon may be transparent. The light fiber may provide light activation through the distal segment, the plurality of serial balloons, and the distal balloon. The plurality of serial balloons may remain in an expanded state when the light fiber provides light activation through the distal segment, the plurality of serial balloons, and the distal balloon. In some embodiments, the plurality of serial balloons remain in an expanded state that casts a treatment shape into the treatment region of the vessel.

Embodiments of the present disclosure provide a method of tissue restoration in a blood vessel of a subject. The method may include providing a catheter into the blood vessel. The catheter may include a catheter shaft extending from a proximal end to a distal tip, a plurality of serial balloons positioned on a translucent distal segment of the catheter shaft proximal to the distal tip and positioned inside of and concentric with a second distal balloon, the plurality of serial balloons in fluid communication with an inflation source via a first lumen, each of the plurality of serial balloons having a selectively expandable outermost radial surface. The plurality of serial balloons may include a translucent material, a series of isolated volumetric regions positioned between the plurality of serial balloons and recessed from the outermost radial surfaces of the serial balloons. The apparatus may include a distal balloon positioned around the plurality of serial balloons, and a light fiber positioned in the catheter shaft and extending through the translucent distal segment. The method may include supplying a drug from the drug source to the infusion ports, delivering the drug to the treatment area through the plurality of apertures, activating the light fiber thereby providing light transmission through the distal segment, the plurality of serial balloons, and the distal balloon to activate the drug in the treatment area.

In some embodiments, the method further includes filling the drug into the isolated volumetric regions between an inside surface of the distal balloon and an outside surface of the plurality of serial balloons. The method may further include inflating the serial balloons into an expanded state during the filling of the isolated volumetric regions. The method may further include casting a treatment shape into a treatment region of the vessel by inflating the plurality of serial balloons into an expanded state. In some embodiments, supplying the drug further includes increasing a pressure of the fluid in the isolated volumetric regions that inflates the distal balloon, the increased pressure delivers the fluid through the apertures.

In some embodiments, the plurality of serial balloons remain in an expanded state that casts a minimal trauma treatment shape into the treatment region of the vessel. The light fiber and the second light fiber may provide light activation through the distal segment, the plurality of serial balloons, and the distal balloon. The method may further include delivering fluid to treatment regions in the treatment area, each treatment region aligned with a respective isolated volumetric region between the plurality of serial balloons.

Embodiments of the disclosure may provide an apparatus. The apparatus may include a catheter shaft extending from a proximal end to a distal tip, a plurality of serial balloons positioned on a translucent distal segment of the catheter shaft proximal to the distal tip and positioned inside of and concentric with a distal balloon, the plurality of serial balloons in fluid communication with an inflation source via a first lumen, each of the plurality of serial balloons having a selectively expandable outermost radial surface. Each of the plurality of serial balloons may include a translucent material, a series of isolated volumetric regions positioned between the plurality of serial balloons and recessed from the outermost radial surfaces of the serial balloons. The apparatus may include a second distal balloon positioned around the plurality of serial balloons, and a light fiber positioned in the catheter shaft and extending through the translucent distal segment. The drug source may be configured to provide at least one drug to the distal balloon via the first lumen and during inflation of the plurality of serial balloons, the fluid fills between an inside surface of the distal balloon and inflation ports, gradually fills the isolated volumetric regions.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

DETAILED DESCRIPTION

Reference will now be made in detail to embodiments and aspects of the present disclosure, examples of which are illustrated in the accompanying drawings. Where possible, the same reference numbers will be used throughout the drawings to refer to the same or like parts.

Figure 1:
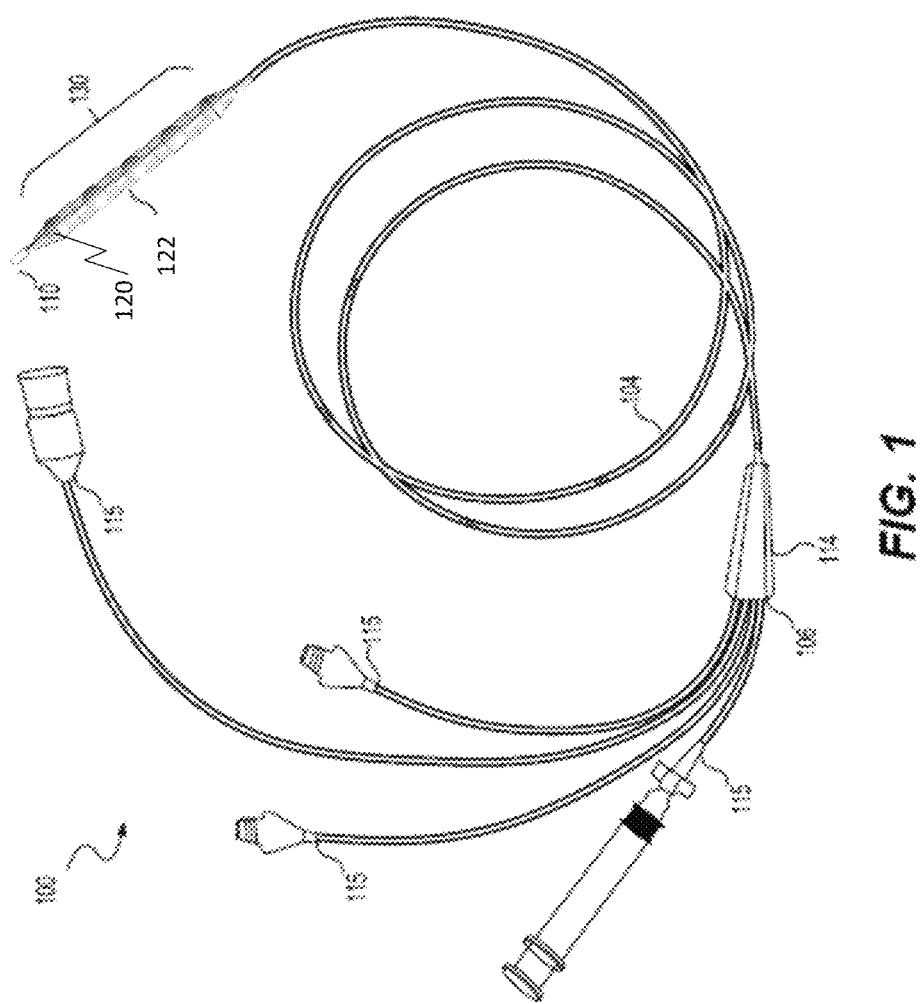
FIG. 1 is a side elevational view of an exemplary apparatus including a catheter, according to embodiments of the present disclosure.

FIG. 1 illustrates an apparatus 100 in accordance with an embodiment of this disclosure. The apparatus 100 having a catheter shaft 104 that extends from a proximal end 106 to a distal tip 110 of the apparatus 100. The apparatus 100 may be configured for longitudinal movement and positioning within a vessel (e.g. blood vessel) of a subject. In some embodiments, the apparatus 100 may be configured for treatment of an area of the vessel. In some embodiments, the apparatus 100 may occlude the vessel, while in other embodiments the apparatus may not occlude the vessel. For example, the apparatus 100 may be configured for delivery of a drug to an area of the vessel occupied by the apparatus 100 which may form and cast a shape in the vessel, as will be described in more detail below.

The apparatus 100 may include a proximal end connector 114 positioned at the proximal end of the apparatus 100, and the catheter shaft 104 may extend in a distal direction therefrom. The catheter shaft 104 may define a plurality of lumens that are accessible via a plurality of ports the proximal end connector 114. The plurality of ports 115 may be configured to engage with external sources desirable to communicate with the plurality of lumens. The ports may engage with external sources via a variety of connection mechanisms, including, but not limited to, syringes, overmolding, quick-disconnect connectors, latched connections, barbed connections, keyed connections, threaded connections, or any other suitable mechanism for connecting one of the plurality of ports to an external source. Non-limiting examples of external sources may include inflation sources (e.g. saline solutions), gaseous sources, treatment sources (e.g. medication, drugs, or any desirable treatment agents discussed further below), light sources, among others. In some embodiments, apparatus 100 can be used with a guide wire (not shown), via guide wire lumen 164 (see FIG. 5A), to assist in guiding the catheter shaft 104 to the target area of the vessel.

FIGS. 1, 2, and 3 illustrate the apparatus 100 including an inner balloon segment 120 positioned inside of and concentric with an outer balloon segment 122 over a distal segment 130 of the catheter shaft 104 proximal to the distal tip 110. In some embodiments, the most distal balloon of the inner balloon segment 120 may be proximally offset from the distal tip 110 a distance between 0 mm and 1 mm, 0 mm and 2 mm, 0 mm and 3 mm, 0 mm and 10 mm, or 0 and 50 mm and may take any shape suitable for supporting a wall of a blood vessel or other hollow body structure of the subject when the inner balloon segment is inflated. The force exerted against a vessel interior by segment 130 may be strong enough to scaffold the vessel wall with the apparatus 100 held in a stationary position within the vessel or other hollow body structure. However, the force is not so great as to damage the interior surface of the vessel or other hollow body structure.

The outer balloon segment 122 may have one continuous surface sealed at each end around the catheter shaft 104 forming an enclosed volume and in fluid communication through a plurality of ports on the catheter shaft 104 through distinct and separate lumens from the inner balloon segment 120. The outer balloon segment 122 may be substantially translucent. In some embodiments, the outer balloon 122 may inflate to 2 to 10 millimeters (mm) in diameter. In other embodiments, the outer balloon 122 may inflate to 1 to 8 cm in diameter. The outer balloon 122 may have a length of about 0.5 to 1 centimeters (cm), 1 to 2 cm, 1 to 3 cm, or 1 to 5 cm, or 1 to 10 cm, or 1 to 15 cm, or 1 to 20 cm, or 1 to 25 cm, and may take any shape suitable for supporting a wall of a blood vessel of the subject when the outer balloon 122 is inflated. For example, the outer balloon 122 may expand into a cylindrical shape surrounding the inner balloon 120 segment of the distal segment 130 of the catheter shaft 104. The cylindrical shape may be gradually tapered inward at a proximal end and a distal end of the inner balloon 120, thereby providing a gradually tapered proximal end and distal end of the outer balloon 122 that taper into contact with and become flush with the catheter shaft 104.

Non-limiting examples of shapes the inflated outer balloon 122 may form include a cylindrical shape, football-shaped, spherical, ellipsoidal, or may be selectively deformable in symmetric or asymmetric shapes so as to limit the potential difference in the treated vessel shape and the untreated vessel shape reducing edge effects common between two surfaces of different stiffness as found in metal stents.

The apparatus 100 may include a plurality of connectors 115 positioned proximally to the proximal end connector 114. For example, the outer balloon 122 may be terminated at the proximal end with a connector capable of receiving a drug source. In some embodiments, the connector may be a luer configuration. The inner balloon segment 120 may be terminated at the proximal end with a separate and distinct connector capable of receiving a fluid for inflation, which may, in some embodiments, be a luer configuration. A center lumen (discussed in more detail below), may be terminated at the proximal end with a connector capable of receiving a fluid source for clearing the lumen from the proximal termination to outside the distal tip, and in some embodiments may include a luer configuration. The center lumen may also accommodate a guidewire for tracking the catheter apparatus to the desired anatomical location. As discussed in more detail below, the apparatus 100 may also include light fibers that may be terminated at the proximal end with an adaptor capable of connecting with a light source. Each light fiber may terminate with a separate and distinct adaptor or each light fiber may share an adaptor to a light source.

The materials of the apparatus 100 may be biocompatible. The catheter shaft 104 may include material that is extrudable and capable of sustaining lumen integrity. The distal segment 130 of the catheter shaft 104 is substantially translucent to allow light transmission from light fibers. The catheter shaft 104 material is rigid enough to track over a guidewire and soft enough to be atraumatic. The catheter shaft 104 may be made of materials including, but not limited to polymers, natural or synthetic rubber, metal and plastic or combinations thereof, nylon, polyether block amide (PEBA), nylon/PEBA blend, thermoplastic copolyester (TPC), a non-limiting example may be HYTREL® (available from Dupont de Nemours, Inc. of Wilmington, Deleware), and polyethylene. The shaft materials can be selected so as to maximize column strength to the longitudinal length of the shaft. Further, the shaft materials can be braided, so as to provide sufficient column strength. The shaft materials can also be selected so as to allow the device to move smoothly along a guide wire. The catheter shaft 104 can also be provided with a lubricious coating as well as antimicrobial and antithrombogenic coatings. The shaft materials should be selected so as not to interfere with the efficacy of the agent to be delivered or collected. This interference may take the form of absorbing the agent, adhering to the agent or altering the agent in any way. The catheter shaft 104 of the present disclosure may be between about 2-16 French units ("Fr." where one French equals ⅓ of a millimeter, or about 0.013 inches). The catheter shafts to be used in coronary arteries may be between about 3-5 Fr. in diameter, and more specifically may be 3 Fr. The catheter shafts to be used in peripheral vessels may be between about 5-8 Fr. in diameter, and more specifically 5 Fr. The catheter shafts to be used in the aorta may be between about 8-16 Fr. in diameter, and more specifically 12 Fr.

The inner balloon segment 120 and the outer balloon 122 may be substantially translucent permitting light from light fibers to be transmitted substantially beyond the inflated diameters of the outer balloon 122. The outer balloon 122 may be compliant such that the material conforms substantially to a vessel's morphology. The inner balloon segment 120 material may be more rigid and noncompliant, capable of higher internal pressures with minimal outward expansion for propping open vessels that are more resistant to pressures. The compliance of the inner balloon segment 120 and outer balloon 122 may be comparable or dissimilar. For example, the inner balloon segment 120 may be non-compliant, capable of higher internal pressures with minimal outward expansion for propping open and casting a vessel into optimal shapes. The inner balloon 122 material may be elastic, capable of covering the inner balloon segment 120 as a skin or covering, expanding and contracting with the inflation of the inner balloon segment 120 and elastically conforming substantially to a vessel's morphology for optimal drug delivery. The outer balloon 122 may include material that conforms to the morphology of the vessel wall thereby providing optimal drug delivery in a non-dilating and non-traumatic manner. The apparatus 100 may not cause any further trauma (e.g. trauma caused by atherectomy or percutaneous transluminal angioplasty "PTA" or vessel preparation methods) to the vessel to promote optimal healing.

The balloons may be thick or thin for performance optimization. The inner balloon segment 120 may be thicker (0.002 inches) to prop the vessel wall for shaping. The outer balloon may be thinner (0.001 inches) to better form the opening and closing function of the perforations 198 described in more detail below.

Figure 3B:
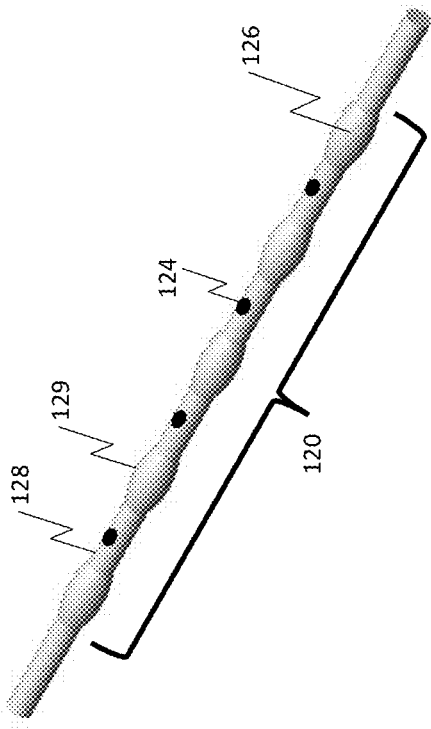
FIGS. 3A and 3B are a perspective view of an exemplary inner balloon of the catheter of FIG. 1; 3A is shown inflated and 3B is shown deflated.
Figure 3A:
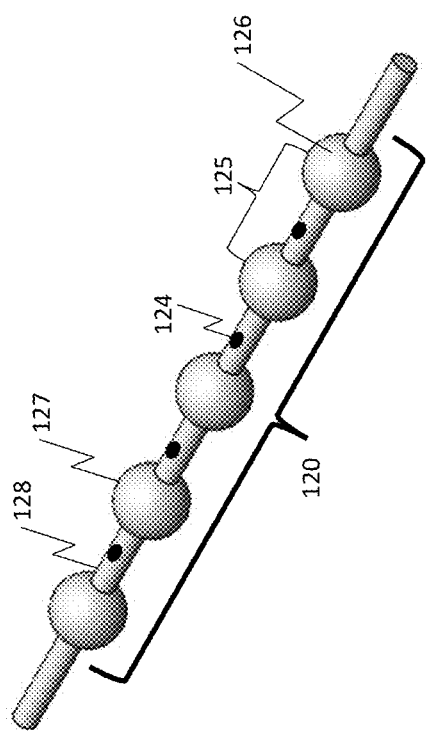

FIG. 3A is a perspective view of the inner balloon segment 120 with the surrounding outer balloon 122 removed. In some embodiments, the inner balloon segment 120 may not be a high-pressure apparatus, but instead the inner balloon segment 120 may be non-dilating and used for vessel shape forming or propping a vessel open. The inner balloon segment 120 includes a plurality of serial balloons 126. The inner balloon segment includes infusion ports 124 between the serial balloons 126 of the inner balloon segment 120. The infusion ports 124 located between each serial balloon 126 of the inner balloon segment 120 form isolated volumetric regions 125 for fluid. The volume is confined by the inner most radial surface 128, the outer surface 127 of the serial balloon 126, and the inner surface 196 of the outer balloon 122.

FIG. 3B is a perspective view of the inner balloon segment 120 with the surrounding outer balloon 122 removed and the serial balloons deflated 129.

Figure 4:
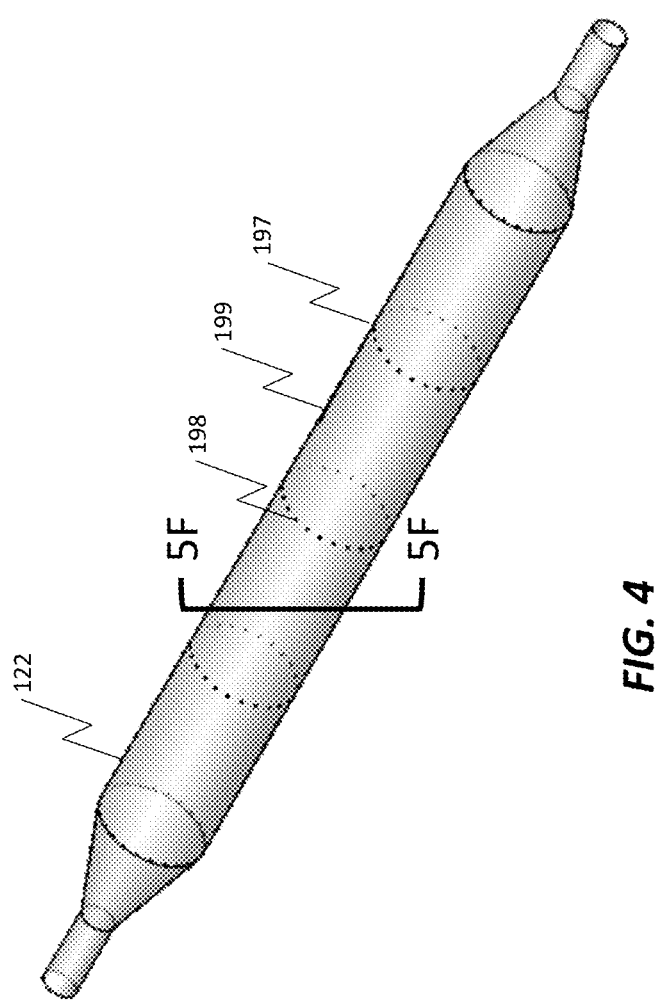
FIG. 4 is a perspective view of an exemplary outer balloon of the catheter of FIG. 1.

FIG. 4 illustrates the outer balloon 122 that may include material that is substantially translucent and elastic, capable of remaining in contact with the outermost radial surface of the inner balloon segment 120, and may act as a covering or skin of the inner balloon segment 120, during inflation and deflation of the inner balloon segment 120. The outer balloon 122 may include a plurality of perforations 198 penetrating through the balloon wall. The perforations 198 may be in fluid communication from the inside surface of the outer balloon 122 to the outside surface of the outer balloon 122, as described in more detail below. The perforations may be formed in an inflated or expanded material state whereupon in a deflated or contracted state the perforations remain naturally closed.

Figure 5C:
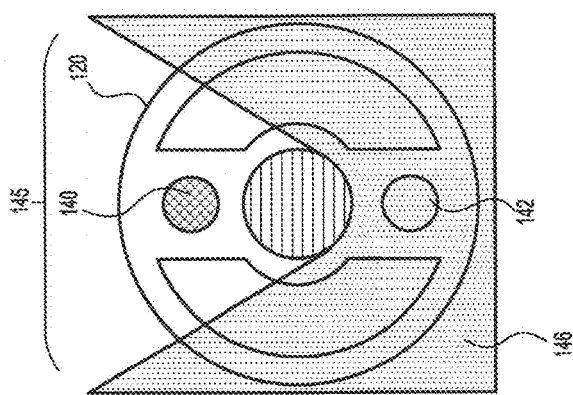
FIGS. 5A, 5B, and 5C are cross-sectional views taken along line 5A-5A of FIG. 2A.
Figure 5B:
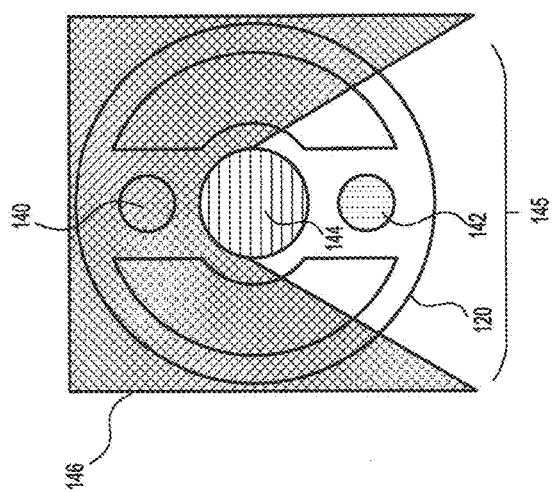
Figure 5A:
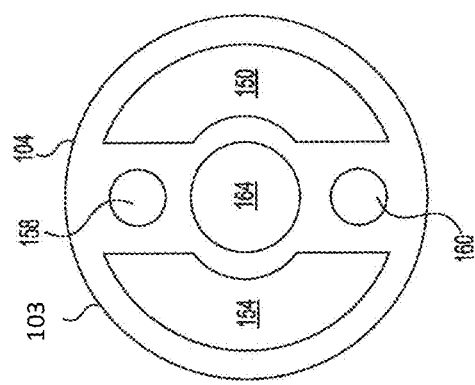

FIG. 5A is a cross-sectional view taken along line 5A-5A of FIG. 2 showing a plurality of lumens within the assembly 100, according to an embodiment of this disclosure. The catheter shaft 104 may have an outside diameter and outside surface 103. The catheter shaft 104 may have an inside configuration of five distinct and separate lumens, extending from the proximal end 106 to the distal tip 110.

The inner balloon segment 120 may be in fluid communication with an inner balloon inflation lumen 150. The outer balloon 122 may be in fluid communication with an outer balloon inflation lumen 154 that is separate and distinct from the inner balloon inflation lumen 150. There may be a plurality of outer balloon inflation lumens (not shown). The inner balloon segment 120 may be in fluid communication with an inflation source via the inner balloon inflation lumen 150 separate from the outer balloon inflation lumen 154. The inner balloon inflation lumen 150 may extend through the catheter shaft 104 and have an input at one of the plurality of ports 115 of the proximal end connector 114. Fluid communication between the inner balloon segment 120 and the inflation source via the inner balloon inflation lumen 150 may cause the inner balloon segment 120 to selectively fill separately from and independently of the outer balloon 122. Similarly, the outer balloon 122 may be in fluid communication with an inflation source via the outer balloon inflation lumen 154 separate from the inner balloon inflation lumen 150. Fluid communication between the outer balloon 122 and the inflation source via the outer balloon inflation lumen 154 may cause the outer balloon 122 to selectively inflate and deflate separately from and independently of the inner balloon segment 120.

A first light fiber lumen 158 and a second light fiber lumen 160 may be positioned in the catheter shaft 104 to receive light fibers, and the first light fiber lumen 158 and the second light fiber lumen 160 may extend from the proximal end 106 into the distal segment 130, and may be positioned substantially symmetric, longitudinally opposed and parallel one to another within the catheter shaft 104. In another exemplary embodiment, the catheter shaft 104 may include a single light fiber lumen. In still other embodiments, the catheter shaft 104 may include a plurality of light fiber lumens.

A guidewire lumen 164 may be concentric with the catheter shaft outside diameter and may be arranged in the catheter shaft 104, from the proximal end 106 through the distal tip 110. The guidewire lumen 164 may accommodate a guidewire to aid the placement of the apparatus 100 to a desired anatomical position communicating with the proximal end and distal tip. The guidewire may be separate and distinct from the apparatus 100 and extend proximally beyond the proximal end and distally beyond the distal tip of the catheter shaft. The guidewire lumen 164 is located concentric with the catheter outer diameter; the catheter shaft is oriented concentrically with the guidewire permitting the catheter shaft 104 to follow the guidewire without favoring one side of the catheter shaft 104 or whipping from side to side. The guidewire may remain in the guidewire lumen 104 maintaining anatomical position during the activation of the light fibers.

FIGS. 5B and 5C illustrate cross-sectional views taken along line 5A-5A of FIG. 2. The apparatus 100 may further include a first light fiber 140 and a second light fiber 142 positioned in the catheter shaft 104 and extending through the distal segment 130. The light fibers 140, 142 may transmit light through the distal segment 130, the outer balloon 122, and the inner balloon segment 120. The light fiber 140 may be connected to the proximal end connector 114 and may have proximal ends that connect to a light fiber activation source via at least one of the plurality of ports 115. In some embodiments, the light fibers 140, 142 may be configured to transmit light at a wavelength of 375 nanometers (nm) to 475 nm, and more specifically 450 nm that transmits through the distal segment 130 and the inner balloon segment 120. The light fibers 140, 142 may emit light outside of the ultraviolet (UV) range of 10 nm to 400 nm. In some embodiments, the light first fiber 140 may be positioned in the first light fiber lumen 158 and the second light fiber 142 may be positioned in the second light fiber lumen 160.

In some embodiments, light from the light fibers 140, 142 may be unable to penetrate through a guidewire 144 forming a shadow 145 opposite the light and beyond the guidewire 144. Accordingly, the light fibers 140, 142 may each generate a respective light transmission area 146. The light fiber lumens 158, 160 are oriented substantially opposite one another minimizing the shadow 145 formed by the light impenetrable guidewire 144, permitting the transmission of light to penetrate the circumference of the catheter shaft 104 from the first light fiber 140 or the second light fiber 142. In another embodiment, the catheter shaft 140 may include a single light fiber, and the guidewire may be removed for light penetration to the outer tissue.

In some embodiments, the light fibers 140, 142 may be made from plastic core and cladding. The refractive index of the core is high. The refractive index of the cladding is low. A non-limiting example of the core material may be polymethyl methacrylate (PMMA). A non-limiting example of the cladding may be a silicone material. The light source may control the wavelength and supplied power of the light fibers 140, 142. The pattern of the breaks in the cladding of the light fiber ensure uniform power distribution to the vessel wall. Longer lengths have a different pattern than shorter lengths. The distal lengths of cladding breaks are matched to the length of the balloons. In other embodiments, the pattern of the breaks in the cladding of the light fiber is the same for different lengths.

Figure 2A:
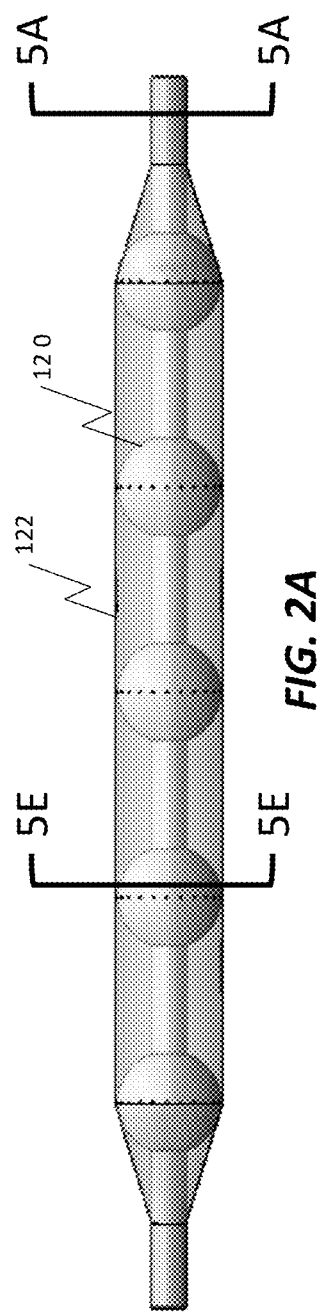
FIG. 2A is a side elevational view of an inflated distal portion of the catheter of FIG. 1 where the perforations of the outer balloon are aligned with the serial balloon surfaces of the inner balloon.
Figure 2B:
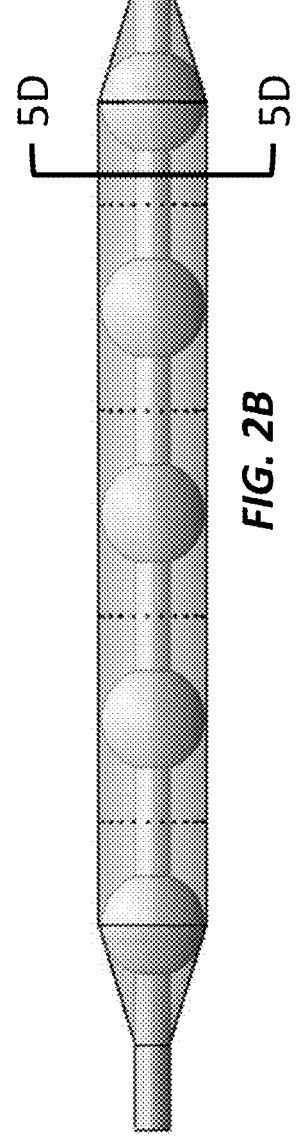
FIG. 2B is a side elevational view of an inflated distal portion of the catheter of FIG. 1 where the perforations of the outer balloon are not aligned with the serial balloon surfaces of the inner balloon.
Figure 5E:
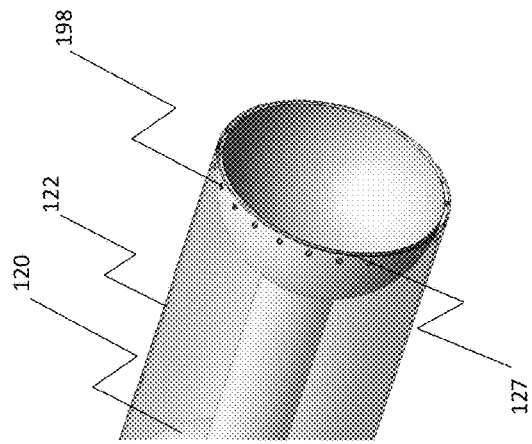
FIGS. 5D, 5E, 5F and 5G are perspective cross-sectional views taken along 5D-5D of FIG. 2B, 5E-5E of FIG. 2A, 5F-5F of FIGS. 4 and 5G-5G of FIG. 2C.
Figure 5G:
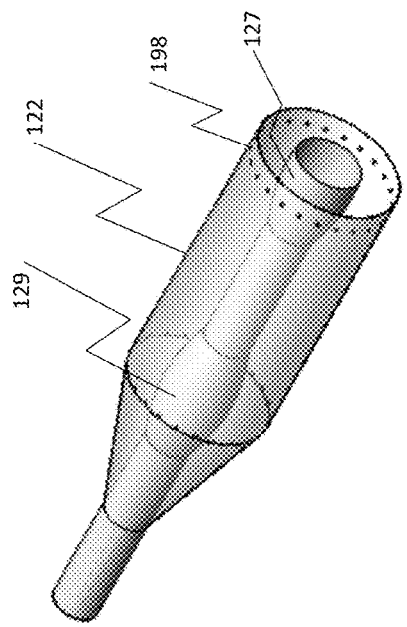
Figure 5D:
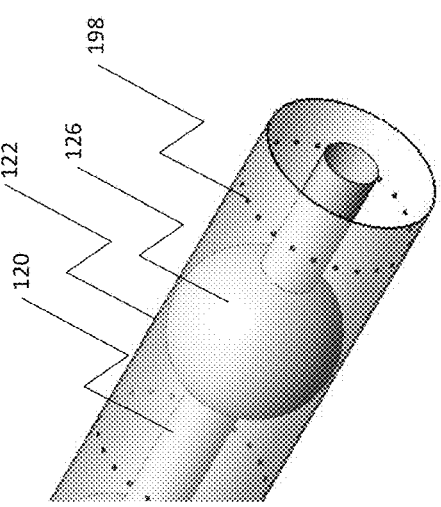

FIG. 5D is a perspective cross-sectional view taken along line 5D-5D of FIG. 2B illustrating the inner balloon segment 120 inflated, the outer balloon 122 inflated and perforations 198 located between the serial balloons 126.

FIG. 5E is a perspective cross-sectional view taken along line 5E-5E of FIG. 2A illustrating the inner balloon segment 120 inflated, the outer balloon 122 inflated and perforations 198 located on the serial balloons surfaces 127.

Figure 5F:
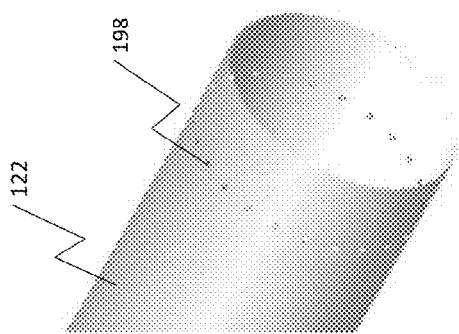

FIG. 5F is a perspective cross-sectional view taken along line 5F-5F of FIG. 4 illustrating the outer balloon 122 inflated and perforations 198.

Figure 2C:
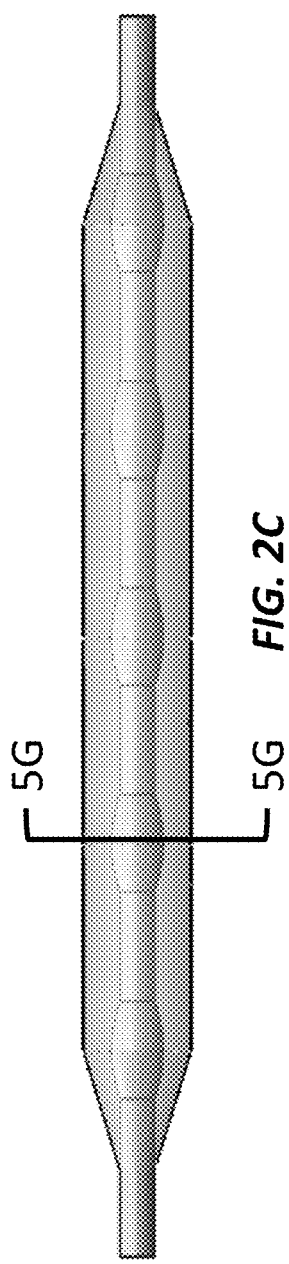
FIG. 2C is a side elevational view of a distal portion of the catheter of FIG. 1 where the perforations of the outer balloon are aligned with the deflated serial balloon surfaces of the inner balloon.

FIG. 5G is a perspective cross-sectional view taken along line 5G-5G of FIG. 2C illustrating the inner balloon segment 120 deflated (serial balloon 129), outer balloon 122 expanded and perforations 198 located on the serial balloons surfaces 127.

Figure 6:
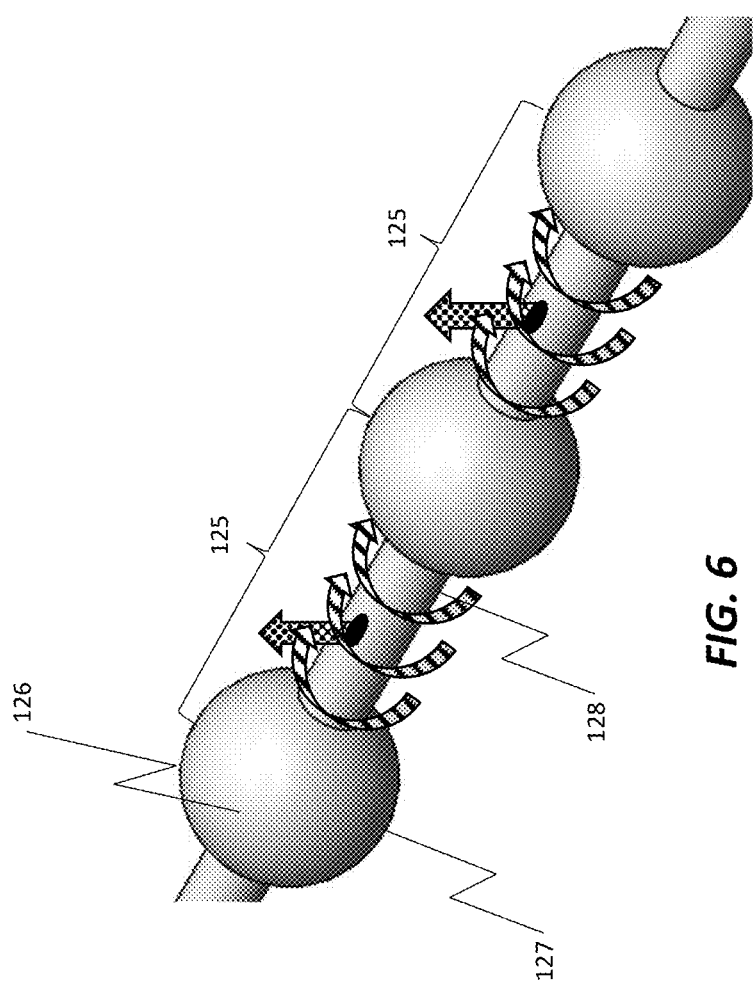
FIG. 6 is a perspective detailed view of the inner balloon of FIG. 3.

As shown in FIG. 6, the inner balloon segment 120 is formed from a plurality of serial balloons 126. The serial balloons 126 may be of one continuous balloon with high (127) and low (128) surfaces or separate and independent balloons individually located and secured to the shaft 104. Separate and independent balloons may reduce costs and improve quality by providing one balloon diameter for a variety of device lengths, reducing the number of parts (one balloon) for each device. Likewise, a single diameter balloon may more easily be inspected and improved than multiple balloons. Also, the assembly of single balloons may more easily be automated and simplified than multiple balloons of various lengths.

The inflated inner balloon segment forms isolated volumetric regions 125 for fluid. The volume is confined by the inner most radial surface 128, the radial outer surface 127 of the serial balloon 126, and the inner surface 196 of the outer balloon 122 (not shown). The volumetric regions are separate and distinct from one another and may or may not share an infusion lumen 154. The same infusion source may flow through the infusion ports 124; however the volumetric regions may be supplied from separate and distinct infusion lumens for infusion efficiency. The innermost radial surfaces 128 permit fluid to fill the volume 125 longitudinally and circumferentially, following the directional arrows, supplying fluid throughout the entire volume 125 and expanding the outer balloon 122. Fluid delivery is achieved when the volume 125 exceeds the outer balloon volume from continual infusion through infusion ports 124 and penetrates through the perforations 198 into the surrounding areas when the perforations 198 of the outer balloon 122 are unaligned with the serial balloons 126 of the inner balloon 120. When the perforations 198 of the outer balloon 122 are aligned with the serial balloons 126 of the inner balloon 120, delivery is achieved by the deflation of the serial balloons, permitting the perforations 198 to be unobstructed by the serial balloon surfaces 127.

Figure 7:
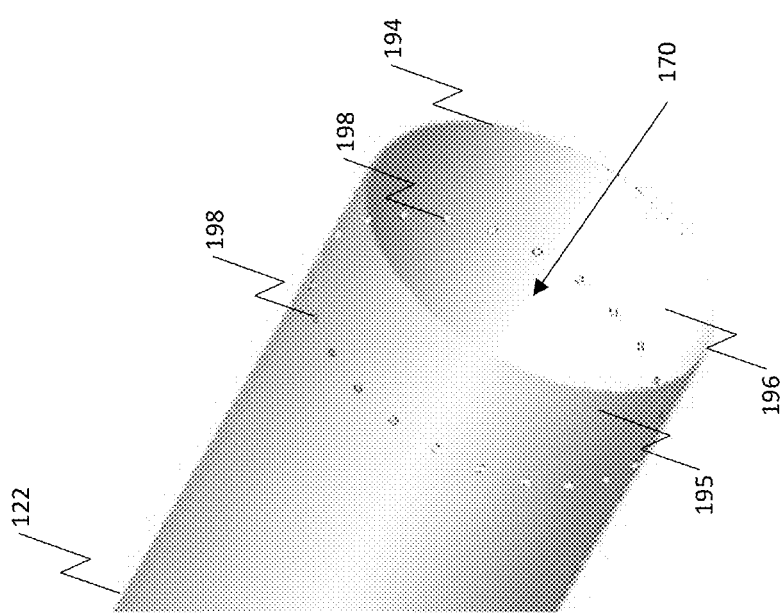
FIG. 7 is a perspective detailed view of the outer balloon of FIG. 4.

FIG. 7 illustrates the outer balloon 122 may have a thickness 194 forming an outside surface 195 and an inside surface 196. The inside surface 196 forms a confined and isolated volume 170 in fluid communication with the proximal end 106 of the catheter shaft 104 and a plurality of perforations 198. The outer balloon 122 may include material that is substantially translucent and elastic, capable of remaining in contact with the outermost radial surface 127 of the inner balloon segment 120, acting as a covering or skin, during inflation and deflation of the outer balloon 122. The outer balloon 122 may include material that is a porous membrane (ePTFE) substantially non-translucent and elastic, capable of permitting substantial light transmittance, and capable of remaining in contact with the outermost radial surface 127 of the inner balloon segment 120, acting as a covering or skin, during inflation and deflation of the outer balloon 122. The outer balloon 122 may include a plurality of perforations 198 which may penetrate through thickness 194 of the wall of the outer balloon 122 in fluid communication from the inside surface 196 of the outer balloon 122 to the outside surface 195 of the outer balloon 122.

The perforations 198 may be obstructed by the serial balloon surface 127 or not obstructed or a combination of both unobstructed and obstructed. In the obstructed position the serial balloon surface 127 must be separated from the inner surface 196 of the outer balloon 122 by further infusion of fluid, expanding the outer balloon and moving the perforations away from the serial balloon surface 127 or by the deflation of the inner balloon segment 120 moving the serial balloon surfaces 127 away from the perforations 198. The plurality of perforations 198 may be of various sizes, shapes, patterns and locations for optimal delivery to the desired anatomy.

Figures 8A, 8B, 8C:
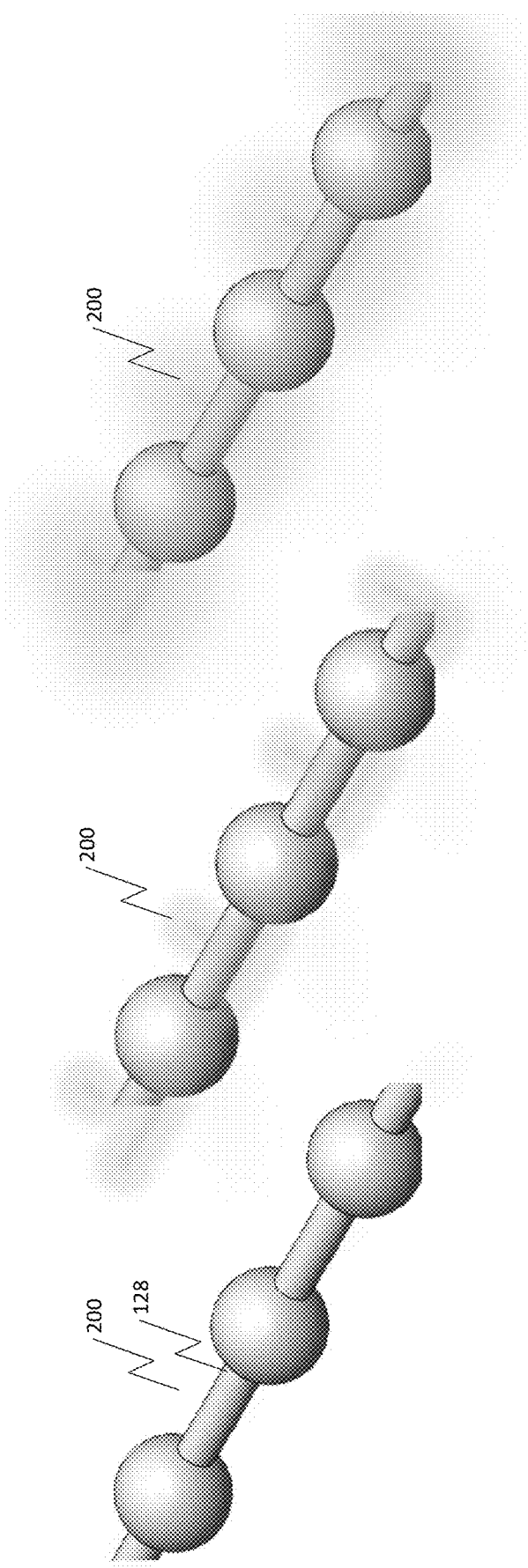
FIGS. 8A-8C show a series of internal perspective views illustrating a filling sequence in accordance with embodiments of the present disclosure.

FIGS. 8A-8C illustrate an progressive inflation sequence in accordance with embodiments of the present disclosure. Although the outer balloon 122 is not specifically shown in FIGS. 8A-8C, the volume 125 between the serial balloons 126 is filled by fluid infused through the infusion ports 124 generating the fluid patterns shown in FIGS. 8A and 8C.

Inflating the inner balloon segment 120 forms substantially invariable volumetric regions 125 covered by the outer balloon 122 which may be elastic. As illustrated in FIGS. 8A-8C, the fluid 200 fills the volumetric regions 125 first. As the volumetric regions 125 fill to capacity, the fluid penetrates through the unobstructed perforations 198 or the inner balloon segment 120 serial balloons 126 are deflated, removing the serial balloon surface 127 from the inner surface 196 of the outer balloon 122. The fluid 200 may be a drug source and provide a therapeutic purpose when functionalized with a light source at the proper wavelength. Inflating and expanding the outer balloon may increase the size of the perforations. Inflating and deflating the outer balloon 122, increasing and decreasing the unobstructed perforations 198 may provide a means to turn delivery on or off, acting as a series of microvalves. Similarly, filling the volumetric region 125 and deflating the inner balloon segment 120 permits fluid delivery. Inflating the inner balloon obstructs the perforations. By inflating and deflating the inner balloon segment 120, a means is provided to turn delivery on or off, acting as a series of microvalves. The volumetric regions permit the infusion of fluid through the entire length of the distal segment 130, priming the device by filling the volumetric regions before the fluid penetrates the perforations 198. In this manner, the sequence of delivery is divided into separate and distinct steps; infusing drug to the entire device length then infusing the drug to the tissue wall. Each volumetric region 125 acts independently in filling. If one volumetric region 125 malfunctioned, other volumetric regions 125 could remain functional. Priming the volumetric regions 125 before fluid delivery ensures uniform delivery of tortuous anatomy or minimizes the loss of fluid in adjacent tributaries when the delivery rate of the perforations are the same.

The target area for a delivery of drug source may be a vessel of the cardiovascular system. The target area may be first prepared by percutaneous transluminal angioplasty (PTA) or atherectomy to displace or remove damaged vessel cellular debris. The catheter apparatus 100 is not intended to replace PTA; the functional pressure of the inner balloon segment 120 is only sufficient to prop open the vessel during drug functionalization. However, the inflation of the inner balloon segment inflates a set of serial balloons spaced apart. Inflated serial balloons produce areas of high stress and low stress in an atherosclerotic vessel. The high stress areas correspond to areas contacted by the serial balloon surface 127. The low stress areas correspond with the volumetric regions 125 and no balloon contact. This variation of high and low stress may fracture the atherosclerosis in a less traumatic manner than conventional means (scoring balloons, PTA, atherectomy, etc.) permitting the delivery device to be first used to produce cracks in the atherosclerosis and subsequently for drug delivery to the same location, simplifying and expediting the treatment procedure. In some embodiments, while the inner balloon segment 120 is inflated, propping open the vessel wall and shaping the vessel diameter, and while the outer balloon 122 is inflated and drug penetrates through the perforations 198 the light source may be activated during drug delivery.

In some embodiments, the apparatus 100 may be capable of delivering two drugs simultaneously. For example, the outside of the outer balloon 122 may be coated with a first drug and a second drug may be delivered through the perforations 198. Accordingly, the first drug and the second drug may be different drugs. In some embodiments, the first drug and the second drug may be the same drug. In a non-limiting example, the outer balloon 122 inner or outer surface may be coated with Paclitaxel and infusing an aqueous drug or saline through the slits to the vessel wall.

While in this vessel supported position, a light source may be supplied to the light fibers 140, 142 in the catheter shaft 104 for transmittance through the catheter shaft 104, through the inner balloon segment 120 and the outer balloon 122, and into the vessel wall as previously described.

There are several combinations for the local delivery of a drug source. For example, a solid drug may be coated on the outside surface of the outer balloon 122 and an aqueous drug may be delivered through the perforations 198 of the outer balloon 122. The drug may be the same, one solid and one aqueous, each penetrating the vessel wall differently. The drugs may be complimentary, but different substances (e.g., one drug may cross-link collagen restoring vessel properties and a complimentary drug may be an antiproliferative reducing procedure related inflammation). The aqueous or solid drug may assist in the capacity of an excipient or activate its counterpart through a controlled reaction. The drugs may be dissimilar and non-complimentary affecting the vessel wall through substantially different methods of action. The drugs may be delivered by the same apparatus (e.g. 100) in sequence, one after the other, or with a timed delay, or multiple times at the same location or at subsequent locations multiple times, permitting the most effective treatment procedure. The drugs may be shone with the light source simultaneously with the delivery (i.e., the light source remains on during the delivery of the drug through the perforations 198). The drugs may be effective when the drugs are near tissue components and functionalized by a light source.

In some embodiments, the drug is not cured or activated, but the drug is functionalized to cross-link with tissue proteins. The tissue proteins, the drug, and the light may be present to create a therapeutic effect. The functionalizing of the drug may not be time dependent, but instantaneous, dependent on wavelength alone. The light power compensates for losses through the light fiber, two balloons, and tissue wall and may be balanced to avoid heat buildup during therapy.

In some embodiments, the apparatus 100 may provide a therapy utilizing multiple aqueous drugs with different methods of action. One drug may be delivered first and functionalized with the light fibers while the vessel is propped open, and subsequently another drug with antiproliferation capabilities may be delivered and not functionalized with the light fibers, and yet another drug with anti-inflammatory properties may be subsequently delivered providing a valuable combination of beneficial drugs without compromising one for the other.

Additionally, therapeutic agents useful with the device of the present disclosure include any one of or a combination of several agents which are gas, liquid, suspensions, emulsions, or solids, which may be delivered or collected from the vessel for therapeutic or diagnostic purposes. Therapeutic agents may include biologically active substances, or substances capable of eliciting a biological response, including, but not limited to endogenous substances (growth factors or cytokines, including, but not limited to basic fibroblast growth factor, acidic fibroblast growth factor, vascular endothelial growth factor, angiogenic factors, microRNA), viral vectors, DNA capable of expressing proteins, sustained release polymers, and unmodified or modified cells. Therapeutic agents may include angiogenic agents which induce the formation of new blood vessels. Therapeutic agents may also include anti-stenosis or anti-restenosis agents which are used to treat the narrowing of blood vessel walls. Therapeutic agents may include light-activated agents such as light-activated anti-stenosis or light-activated anti-restenosis agents that may be used to treat the narrowing of blood vessel walls.

Accordingly, apparatus 100 is multifunctional, providing drug delivery control in open and closed positions, and propping open a vessel wall forming a shape during drug functionalizing with a light source of a specific wavelength outside of the ultraviolet (UV) range (10 nm to 400 nm).

Another embodiment of this disclosure includes an exemplary method of tissue restoration in a blood vessel of a subject. The method may include providing a catheter into the blood vessel. In some embodiments, the catheter may include the features of apparatus 100 described above. For example, the catheter may include a catheter shaft (e.g. catheter shaft 104) extending from a proximal end (e.g. proximal end 106) to a distal tip (e.g. distal tip 110). A first distal balloon (e.g. inner balloon segment 120) may be positioned on a translucent distal segment (e.g. distal segment 130) of the catheter shaft proximal to the distal tip, the first distal balloon in fluid communication with a drug source via a first lumen (e.g. first distal balloon inflation lumen 150). The first distal balloon may include a translucent material and be positioned inside of an concentric with a second distal balloon (e.g. outer balloon 122), a plurality of serial balloons forming volumetric regions (e.g. serial balloons 126, volumetric regions 125). The second distal balloon (e.g. outer balloon 122) may be in fluid communication with a second lumen (e.g. outer balloon inflation lumen 154) separate from the first lumen. The catheter may further include a first light fiber (e.g. light fiber 140) and a second light fiber (e.g. light fiber 142) each positioned in the catheter shaft and extending through the translucent distal segment.

The method may further include supplying a drug from the drug source to the first distal balloon, delivering the drug to the treatment area through the perforations (e.g. perforations 198), activating the first light fiber and the second light fiber, thereby providing light transmission through the distal segment, the first distal balloon, and the second distal balloon to activate the drug in the treatment area. The light transmission to the treatment area may activate the NVS, which may be activated by light. The expansion of the first distal balloon may shape the treatment area (e.g. vessel) as desired.

The method may further include gradually filling the drug into a volumetric regions of the second distal balloon and an outside surface of the first distal balloon, and expanding the second distal balloon, thereby moving the perforations away from the outermost radial surfaces of the serial balloons of the first distal balloon.

Accordingly, the apparatus and methods described herein provide the delivery of NVS to a treatment area (e.g. a vessel) and provide restoration to that treatment area using the apparatus or according to the methods described above. The apparatus and method described above provide concurrently treating the vessel with one or more drugs (e.g. with Paclitaxel and NVS) with minimal loss to other vessels, scaffolding and casting the vessel, and light activation of the one or more drugs delivered to the treatment area. These advantages can be accomplished utilizing the apparatus and methods described herein.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or"

unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure (e.g., slitted apertures, apertures, perforations may be used interchangeably maintaining the true scope of the embodiments)

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. An apparatus comprising:
   a catheter shaft extending from a proximal end to a distal tip;
   a plurality of serial balloons positioned on a translucent distal segment of the catheter shaft proximal to the distal tip and positioned inside of and concentric with a distal balloon, the plurality of serial balloons in fluid communication with an inflation source via a first lumen, each of the plurality of serial balloons having a selectively expandable outermost radial surface and the plurality of serial balloons comprising:
   a translucent material; and
   a series of isolated volumetric regions, one of each of the series of isolated volumetric regions being positioned between adjacent balloons of the plurality of serial balloons and recessed from the outermost radial surfaces of the plurality of serial balloons;
   the distal balloon positioned around the plurality of serial balloons; and
   a light fiber positioned in the catheter shaft and extending through the translucent distal segment,
   wherein the distal balloon comprises a plurality of apertures radially aligned with the isolated volumetric regions of the plurality of serial balloons.

2. The apparatus of claim 1, wherein the apertures selectively communicate a drug from the distal balloon to a treatment area of a subject.

3. The apparatus of claim 2, wherein the apertures provide uniform drug delivery to the series of isolated volumetric regions within the treatment area.

4. The apparatus of claim 3, wherein the plurality of serial balloons remain in an expanded state during drug delivery to the series of isolated volumetric regions.

5. The apparatus of claim 2, wherein during inflation of the distal balloon, the drug fills between an inside surface of the distal balloon and an outside surface of the infusion ports, filling the series of isolated volumetric regions.

6. The apparatus of claim 5, wherein a pressure of the drug in the series of isolated volumetric regions increases and inflates the distal balloon, the increased pressure delivers the drug through the apertures.

7. The apparatus of claim 1, wherein the plurality of serial balloons comprise a plurality of infusion ports, and wherein each infusion port is positioned between adjacent balloons of the plurality of serial balloons.

8. The apparatus of claim 1, wherein the translucent material of the distal segment, the plurality of serial balloons, and the distal balloon are transparent.

9. The apparatus of claim 1, wherein the light fiber provides light activation through the distal segment, the plurality of serial balloons, and the distal balloon.

10. The apparatus of claim 1, wherein the plurality of serial balloons remain in an expanded state when the light fiber provides light activation through the distal segment, the plurality of serial balloons, and the distal balloon.

11. The apparatus of claim 1, wherein the plurality of serial balloons remain in an expanded state that casts a treatment shape into a treatment region of the vessel.

12. A method of tissue restoration in a blood vessel of a subject comprising:
   providing a catheter into the blood vessel, the catheter comprising:
   a catheter shaft extending from a proximal end to a distal tip;
   a plurality of serial balloons positioned on a translucent distal segment of the catheter shaft proximal to the distal tip and positioned inside of and concentric with a distal balloon, the plurality of serial balloons in fluid communication with an inflation source via a first lumen, each of the plurality of serial balloons having a selectively expandable outermost radial surface and each of the plurality of serial balloons comprising:
   a translucent material;
   a series of isolated volumetric regions, one of each of the series of isolated volumetric regions being positioned between adjacent balloons of the plurality of serial balloons and recessed from the outermost radial surfaces of the plurality of serial balloons;
   a plurality of infusion ports, each infusion port being positioned between the plurality of serial balloons
   the distal balloon positioned around the plurality of serial balloons, the distal balloon further comprising a plurality of apertures radially aligned with the isolated volumetric regions of a first distal balloon; and
   a light fiber positioned in the catheter shaft and extending through the translucent distal segment;
   supplying a drug from a drug source to the plurality of infusion ports;
   delivering the drug to a treatment area through the plurality of apertures;
   activating the light fiber thereby providing light transmission through the distal segment, the plurality of serial balloons, and the distal balloon to activate the drug in the treatment area.

13. The method of claim 12 further comprising:
filling the drug into the isolated volumetric regions between an inside surface of the distal balloon and an outside surface of the plurality of serial balloons.

14. The method of claim 13, further comprising inflating the plurality of serial balloons into an expanded state during the filling of the isolated volumetric regions.

15. The method of claim 12, wherein the treatment area further comprises a treatment region, and wherein the method further comprises casting a treatment shape into the treatment region of the vessel by inflating the plurality of serial balloons into an expanded state.

16. The method of claim 15, wherein the supplying the drug further comprises increasing a pressure of the drug in the isolated volumetric regions that inflates the distal balloon, and wherein the increased pressure delivers the drug through the plurality of apertures.

17. The method of claim 12, wherein the plurality of serial balloons remain in an expanded state that casts a minimal trauma treatment shape into a treatment region of the vessel.

18. The method of claim 12, wherein the light fiber and a second light fiber provide light activation through the distal segment, the plurality of serial balloons, and the distal balloon.

19. The method of claim 12, further comprising delivering the drug to treatment regions in the treatment area, each treatment region aligned with a respective isolated volumetric region between the plurality of serial balloons.

20. An apparatus comprising:
a catheter shaft extending from a proximal end to a distal tip;
a plurality of serial balloons positioned on a translucent distal segment of the catheter shaft proximal to the distal tip and positioned inside of and concentric with a distal balloon, the plurality of serial balloons in fluid communication with an inflation source via a first lumen, each of the plurality of serial balloons having a selectively expandable outermost radial surface and each of the plurality of serial balloons comprising:

a translucent material; and
a series of isolated volumetric regions, one of each of the series of isolated volumetric regions being positioned between adjacent balloons of the plurality of serial balloons and recessed from the outermost radial surfaces of the plurality of serial balloons;

the distal balloon positioned around the plurality of serial balloons; and a light fiber positioned in the catheter shaft and extending through the translucent distal segment;

wherein a drug source is configured to provide at least one drug to the distal balloon via the first lumen coincident with inflation of the plurality of serial balloons, and wherein the drug fills between an inside surface of the distal balloon and inflation ports, gradually filling the series of isolated volumetric regions.

* * * * *